United States Patent [19]

Houghton et al.

[11] Patent Number: 5,968,775
[45] Date of Patent: Oct. 19, 1999

[54] HEPATITIS C VIRUS INFECTED CELL SYSTEMS

[75] Inventors: Michael Houghton, Oakland; Kathelyn S. Steimer; Amy J. Weiner, both of Benicia, all of Calif.

[73] Assignee: Chiron Corporation, Emeryville, Calif.

[21] Appl. No.: 08/438,435

[22] Filed: May 10, 1995

Related U.S. Application Data

[62] Continuation of application No. 08/097,853, Jul. 27, 1993, Pat. No. 5,679,342, which is a continuation-in-part of application No. 07/611,965, Nov. 8, 1990, abandoned, which is a continuation-in-part of application No. 07/398,667, Aug. 25, 1989, abandoned, and a continuation-in-part of application No. 07/456,637, Dec. 21, 1989, abandoned, and a continuation-in-part of application No. 07/355,002, May 18, 1989, abandoned, and a continuation-in-part of application No. 07/355,961, May 18, 1989, abandoned, which is a continuation-in-part of application No. 07/341,334, Apr. 20, 1989, abandoned, which is a continuation-in-part of application No. 07/353,896, filed as application No. PCT/US88/04125, Nov. 18, 1988, abandoned, and a continuation-in-part of application No. 07/325,338, Mar. 17, 1989, abandoned, which is a continuation-in-part of application No. 07/271,450, Nov. 14, 1988, abandoned, which is a continuation-in-part of application No. 07/263,584, Oct. 26, 1988, abandoned, which is a continuation-in-part of application No. 07/191,263, May 6, 1988, abandoned, which is a continuation-in-part of application No. 07/161,072, Feb. 26, 1988, abandoned, which is a continuation-in-part of application No. 07/139,886, Dec. 30, 1987, abandoned, which is a continuation-in-part of application No. 07/122,714, Nov. 18, 1987, abandoned.

[51] Int. Cl.$^6$ .................................................. C12Q 1/70
[52] U.S. Cl. ........................... 435/69.3; 435/5; 435/70.1; 435/70.3; 435/91.1; 435/91.33; 435/235.1; 435/240.2; 435/240.27; 435/239; 424/93.21; 424/189.1; 424/228.1
[58] Field of Search .............................. 435/5, 7.21, 7.92, 435/41, 69.3, 70.1, 70.3, 91.1, 91.33, 235.1, 239, 240.2, 240.27, 975; 530/228; 536/23.72; 436/512, 518; 424/156.1, 161.1, 189.1, 228.1, 93.21

*Primary Examiner*—Christine M. Nucker
*Assistant Examiner*—Laurie Scheiner
*Attorney, Agent, or Firm*—Alisa A. Harbin; Kenneth M. Goldman; Robert P. Blackburn

[57] ABSTRACT

The present invention is directed to extracorporeal cell systems infected with hepatitis C virus (HCV). The present invention also relates to products of such cell systems and their use as vaccines and in immunoassays. Methods whereby HCV-infected extracorporeal cell systems are constructed are included, and various immunoassays to detect HCV antibodies are also presented. The HCV-infected cell systems can be used to screen putative antiviral agents.

5 Claims, 6 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

CCCAACACTA CTCGGCTA                                                       18

(2) INFORMATION FOR SEQ ID NO:2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

ACCATGAATC ACTCCCCT                                                       18

(2) INFORMATION FOR SEQ ID NO:3:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

CCATAGTGGT CTGCGGAACC GGTGAGTACA                                          30

HEPATITIS C VIRUS INFECTED CELL SYSTEMS

CROSS-REFERENCES TO RELATED APPLICATIONS

This application is a continuation, of application Ser. No. 08/097,853, filed Jul. 27, 1993, now U.S. Pat. No. 5,679,342, Which is a continuation-in-part of (U.S. Ser. No. 07/611,965) filed Nov. 8, 1990, now abandoned, which is a continuation-in-part of U.S. Ser. No. 07/398,667) filed Aug. 25, 1989 (now abandoned); and also of (U.S. Ser. No. 07/456,637) filed Dec. 21, 1989 now abandoned; (U.S. Ser. No. 07/355,002) filed May 18, 1989, now abandoned and of (U.S. Ser. No. 07/355,961) filed May 18, 1989, now abandoned,; which are continuations-in-part of (U.S. Ser. No. 07/341,334) filed Apr. 20, 1989, now abandoned,; which is a continuation-in-part of PCT US88/04125) filed Nov. 18, 1988, converted to U.S. National phase on Apr. 21, 1989 and designated (U.S. Ser. No. 07/353,896) now abandoned, and a continuation-in-part of (U.S. Ser. No. 07/325,338) filed Mar. 17, 1989 (now abandoned); which are continuations-in-part of (U.S. Ser. No. 07/271,450) filed Nov. 14, 1988 (now abandoned); which is a continuation-in-part of (U.S. Ser. No. 07/263,584) filed Oct. 26, 1988 (now abandoned); which is a continuation-in-part of (U.S. Ser. No. 07/191,263) filed May 6, 1988 (now abandoned); which is a continuation-in-part of (U.S. Ser. No. 07/161,072) filed Feb. 26, 1988 (now abandoned); which is a continuation-in-part of (U.S. Ser. No. 07/139,886) filed Dec. 30, 1987 (now abandoned); which is a continuation-in-part of (U.S. Ser. No. 07/122,714) filed Nov. 18, 1987 (now abandoned). The aforementioned applications are, in their entirety, incorporated herein by reference.

BACKGROUND OF THE INVENTION

1. Field of the Disclosure

The present invention relates to cellular propagation of hepatitis C virus (HCV) and the uses of HCV antigen produced in such cell systems.

2. Description of Related Art

Non-A, Non-B hepatitis (NANBH) is a transmissible disease (or family of diseases) that is believed to be virally induced, and is distinguishable from other forms of virus-associated liver disease, such as those caused by hepatitis A virus (HAV), hepatitis B virus (HBV), delta hepatitis virus (HDV), cytomegalovirus (CMV), or Epstein-Barr virus (EBV). Epidemiologic evidence suggests that there may be three types of NANBH: the water-borne epidemic type; the blood or needle associated type; and the sporadically occurring community acquired type. However, the number of causative agents is unknown.

Recently, however, a new viral species, hepatitis C virus (HCV) has been identified as the primary (if not only) cause of blood-associated NANBH (BB-NANBH). In 1987, scientists at Chiron Corporation (the assignee of the present application) identified the first nucleic acid definitively linked to blood-borne NANBH. See, e.g., EPO Pub. No. 318,216 (published May 31, 1989) and EPO Pub. No. 388,232 (published Sep. 19, 1990) or PCT Publ. No. WO 90/11089 (published Oct. 4, 1990).

Hepatitis C appears to be the major form of transfusion-associated hepatitis in a number of countries, including the United States and Japan. There is also evidence implicating HCV in induction of hepatocellular carcinoma. Thus, a need exists for an effective method for preventing and treating HCV infection: currently, there is none.

The demand for sensitive, specific methods for screening and identifying carriers of NANBV and NANBV-contaminated blood or blood products is significant. Post-transfusion hepatitis (PTH) occurs in approximately 10% of transfused patients, and NANBH accounts for up to 90% of these cases. The major problem in this disease is the frequent progression to chronic liver damage (25–55%).

Patient care, as well as the prevention of transmission of NANBH by blood and blood products or by close personal contact, requires reliable diagnostic and prognostic tools to detect nucleic acids, antigens, and antibodies related to NANBV. In addition, there is also a need for effective vaccines and immunotherapeutic therapeutic agents for the prevention and/or treatment of the disease.

Prior to the work performed through applicants' assignee, no etiologic agent for NANBH was identified. See, e.g., U.S. Pat. No. 4,952,494 relating to an assay to detect the presence of live NANBHV in vitro wherein mononuclear cells from bone marrow or peripheral blood are enriched with a growth factor and then incubated with a sample to be tested, and the number of colonies arising from incubation are counted and compared to a control; the presence of live hepatitis virus is related to the inhibition of colony growth; PCT Pub. No. WO 87/05930 (published Oct. 8, 1987), reporting triomas consisting of immortalized non-lymphocytic, non-malignant, human or non-human primate cell lines, including hepatocytes, central nervous system cells, and synovial cells, fused with mouse/human hybridomas, which are then infected with a purported etiologic agent of NANBH; and Hellings, et al., *J. Virol. Method.* 10:321–326 (1985), reporting that a preparation containing mono-nuclear leukocytes, which purportedly were mainly lymphocytes, isolated from a patient with NANBH, caused NANBH when infused into a susceptible chimpanzee.

More recent publications of interest include Jacob, et al., *J. Infect. Dis.* 161:1121–1127 (1990); and Jacob, et al., Abstract 490 of The 1990 International Symposium on Viral Hepatitis and Liver Disease, Apr. 4–8, 1990.

SUMMARY OF THE INVENTION

The present invention is directed to extracorporeal cell systems infected with hepatitis C virus (HCV). The present cell systems can include cells of mammalian, particularly primate and more particularly human, origin. Examples of preferred cells include, but are not limited to, hepatocytes; macrophages, more preferably Kupffer macrophages; and B lymphocytes. Furthermore, HCV polypeptide-containing fractions of cell lysates, whole cells, and cell culture supernatants of these cell systems are included herein and can be employed in vaccines and immunoassays of the present invention.

Methods for producing HCV-infected extracorporeal cell systems are detailed herein and comprise: (a) providing an extracorporeal cell system capable of being infected by HCV; (b) providing a source of infective HCV; and (c) infecting the cell system of (a) with the infective HCV of (b) under conditions that allow cell system infection. A preferred cell system comprises hepatocytes infected in a serum-free medium.

Methods for producing HCV-infected extracorporeal cell systems also comprise: (a) providing an extracorporeal cell system capable of being infected by HCV; (b) providing an RNA reagent comprising full-length HCV RNA; and (c) transfecting the cell system of step (a) with the RNA reagent of step (b) under conditions that allow cell transfection. In a preferred embodiment, the RNA reagent of step (b) also contains a 5'-truncated HCV RNA for co-transfection. A preferred cell system for this transfection method is the HUH7 hepatocyte cell line.

Also included are immunoassays for detecting antibodies directed against an HCV antigen comprising:(a) incubating a biological sample suspected of containing anti-HCV antibodies with a HCV-infected extracorporeal cell system product selected from the group consisting of HCV polypeptide-contaning fractions of cell lysates, whole cells, and cell culture supernatants, under conditions that allow the formation of an antibody-antigen complex; and (b) detecting the antibody-antigen complex. A preferred immunoassay is a Western Blot.

Furthermore, methods for screening putative antiviral agents that inhibit HCV infection are described herein and comprise: (a) providing a composition comprised of a putative antiviral agent; (b) providing an extracorporeal cell system capable of being infected by HCV; (c) providing a biological sample containing infective HCV; (d) incubating the compositions of (a) and (c) with the cell system of (b) under conditions that would, in the absence of (a), allow infection of HCV in the cell system; and (e) detecting inhibition of viral infection after incubation. Preferred cell systems include, but are not limited to, hepatocytes; macrophages, more preferably Kupffer macrophages; and B lymphocytes.

Additionally, putative antiviral agents that inhibit HCV replication in HCV-infected cell systems can be screened using present methods that comprise: (a) providing a putative antiviral agent; (b) providing a HCV-infected extracorporeal cell system; (c) incubating the compositions of (a) and (b) under conditions that would, in the absence of (a), allow replication of HCV in the cell line; and (d) detecting inhibition of viral replication after incubation.

Methods for propagating HCV in cell culture are also described and comprise: (a) providing a cell that expresses a receptor selected from the group consisting of the mannose receptor and the asialoglycoprotein receptor; (b) infecting the cell with HCV; and (c) culturing the infected cell. Preferably, the cell expresses a recombinant receptor.

The present invention has utility in the diagnosis, treatment, and prevention of hepatitis C. The cell HCV-infected extracorporeal cell systems can produce HCV polypeptide-containing fractions of cell lysates, whole cells, lysates, and cell culture supernatants constituting a source of viral antigen useful in immunoassays to detect HCV antibodies and in immunogenic or vaccine preparations. HCV-infected cell systems also can be used in screening programs to develop antiviral agents for treating HCV. Antiviral agents may block infection of the cell systems or may prevent viral replication in infected cells.

DETAILED DESCRIPTION OF THE INVENTION

I Defintions

Figure 1:
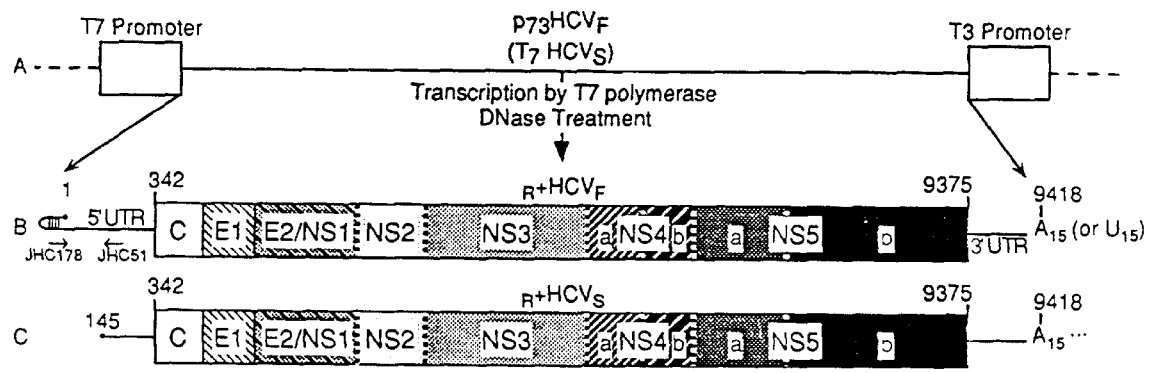
FIG. 1 shows a diagram of the synthetic HCV RNA. Transcription vectors (A) are for the synthesis of full-length HCV RNA (B) and subgenomic HCV RNA (C). The relative position of the two PCR primers JHC 178 and JHC 51 are indicated.

The term "hepatitis C virus" or "HCV" has been reserved by workers in the field for an heretofore unknown etiologic agent of NANBH. Accordingly, hepatitis C virus refers to an agent causative of NANBH, which was formerly referred to as NANBV and/or BB-NANBV. The terms HCV, NANBV, and BB-NANBV are used interchangeably herein. As an extension of this terminology, the disease caused by HCV, formerly called NANB hepatitis (NANBH), is called hepatitis C. The disease terms NANBH and hepatitis C may be used interchangeably herein.

HCV is a viral species of which pathogenic strains cause hepatitis C. The HCV genome is comprised of RNA, and it is known that RNA containing viruses have relatively high rates of spontaneous mutation, i.e., reportedly on the order of $10^{-3}$ to $10^{-4}$ per incorporated nucleotide, see Fields & Knipe, FUNDAMENTAL VIROLOGY, Raven Press, New York (1986). Therefore, there can be multiple strains, which may be virulent, avirulent, or attenuated, within the HCV species. It is believed that HCV is a Flavi-like virus. The morphology and composition of Flavivirus particles are known, and are discussed in Brinton, in THE VIRUSES: THE TOGAVIRIDAE AND FLAVIVIRIDAE (ed. Schlesinger, et al.), pages 327–274, Plenum Press, New York (1986).

Generally, with respect to morphology, Flaviviruses contain a central nucleocapsid surrounded by a lipid bilayer.

Virions are spherical and have a diameter of about 40–50 nm. Their cores are about 25–30 nm in diameter. Along the outer surface of the virion envelope are projections that are about 5–10 nm long with terminal knobs about 2 nm in diameter.

cDNAs to the genome of a prototype strain of HCV, denoted HCV1, as well as to other HCV strains or isolates, are described in U.S. Ser. No. 07/355,002, which is owned by the present assignee, See also EPO Pub. No. 318,216 (published May 31, 1989); EPO Pub. No. 388,232 (published Sep. 19, 1990) or PCT Pub. No. WO 90/11089 (published Oct. 4, 1990); and PCT App. No. US/88/04125 (filed Nov. 18, 1989 and converted to U.S. National phase on Apr. 21, 1989 and designated attorney docket U.S. Ser. No. 07/353,896), which are also owned by the present assignee. Different strains or isolates of HCV are expected to contain variations at the amino acid and nucleic acids levels compared with HCV1. Many isolates are expected to show much (i.e., more than about 40%) homology in the total amino acid sequence compared with HCV1. However, it may also be found that other less homologous HCV isolates would be defined as HCV strains according to various criteria such as an open reading frame (ORF) encoding a polyprotein similar in size to that of HCV1, an encoded polyprotein of similar hydrophobic and antigenic character to that of HCV1, and the presence of co-linear peptide sequences that are conserved with HCV1.

HCV1 encodes at least one epitope that is immunologically identifiable with an epitope encoded in other HCV strains. The epitope is unique to HCV when compared to other known Flaviviruses. The uniqueness of the epitope may be determined by its immunological reactivity with anti-HCV antibodies and lack of immunological reactivity with antibodies to other Flavivirus species. Methods for determining immunological reactivity are known in the art, for example, by radioimmunoassay, by enzyme-linked immunosorbent assay (ELISA), and by hemagglutination. Examples of suitable techniques for determining immunological reactivity of HCV epitopes are described in U.S. Ser. No. 07/341,334; in Choo, et al., Science 244:359 (1989); and in Kuo, et al., Science 244:362 (1989).

In addition to the above, the following parameters of nucleic acid homology and amino acid homology are applicable, either alone or in combination, in identifying a strain or isolate as HCV. Because HCV strains and isolates are evolutionarily related, it is expected that the overall homology of the genomes at the nucleotide level probably will be about 40% or greater, probably about 60% or greater, and even more probably about 80% or greater; and, in addition, that there will be corresponding contiguous sequences of at least about 13 nucleotides. The correspondence between the putative HCV strain genomic sequence and the HCV1 cDNA sequence can be determined by techniques known in the art. For example, they can be determined by a direct comparison of the sequence information of the polynucleotide from the putative HCV, and the HCV cDNA sequence(s) described in U.S. Ser. No. 07/355,002 and EPO Publ. No. 388,232. They also can be determined, for example, by hybridization of the polynucleotides under conditions that form stable duplexes between homologous regions (e.g., those which would be used prior to $S_1$ digestion), followed by digestion with single-stranded specific nuclease(s), followed by size determination of the digested fragments.

Because of the evolutionary relationship of the strains or isolates of HCV, putative HCV strains or isolates are also identifiable by their homology at the polypeptide level. Generally, HCV strains or isolates are expected to be more than about 40% homologous, probably more than about 70% homologous, and even more probably more than about 80% homologous, and some may even be more than about 90% homologous at the polypeptide level. The techniques for determining amino acid sequence homology are known in the art. For example, the amino acid sequence may be determined directly and compared to known sequences. Alternatively the nucleotide sequence of the genomic material of the putative HCV may be determined (usually via a cDNA intermediate), the amino acid sequence encoded therein can be determined, and the corresponding regions compared.

As used herein, the term "viral RNA", which includes HCV RNA, refers to RNA from the viral genome, fragments thereof, transcripts thereof, and mutant sequences derived therefrom.

As used herein, "purified HCV" refers to a preparation of HCV that has been isolated from the cellular constituents with which the virus normally associates, and from other types of viruses that may be present in the infected tissue. The techniques for isolating viruses are known to those of skill in the art, and include, for example, centrifugation and affinity chromatography.

As used herein, a "positive-stranded genome" of a virus is one in which the genome, whether RNA or DNA, is single-stranded and encodes a viral polypeptide(s). Examples of positive-stranded RNA viruses include Togaviridae, Coronaviridae, Retroviridae, Picomaviridae, and Caliciviridae. Included also, are the Flaviviridae, which were formerly classified as Togaviridae. See Fields & Knipe, FUNDAMENTAL VIROLOGY, Raven Press, New York (1986).

As used herein, a "replicative intermediate" of an HCV genome refers to an RNA strand or fragment thereof, which is complementary to the viral genome, and which is synthesized during the course of viral replication; the replicative intermediate functions as a template for the synthesis of plus RNA strands.

The term "polypeptide" refers to a polymer of amino acids and does not refer to a specific length of the product; thus, peptides, oligopeptides, and proteins are included within the definition of polypeptide. This term also does not refer to, or exclude, post-expression modifications of the polypeptide, for example, glycosylations, acetylations, phosphorylations, and the like.

"Immunologically identifiable with/as" refers to the presence of epitope(s) and polypeptides(s) that are also present in the designated polypeptide(s), herein usually HCV proteins. Immunological identity may be determined by antibody binding and/or competition in binding; these techniques are known to those of average skill in the art.

As used herein, "epitope" refers to an antigenic determinant of a polypeptide; an epitope can comprise 3 or more amino acids in a spatial conformation unique to the epitope. Generally an epitope consists of at least 5 such amino acids and, more usually, consists of at least 8–10 such amino acids. Methods of determining the spatial conformation of amino acids are known in the art, and include, for example, x-ray crystallography and 2-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

As used herein, the term "immunogenic polypeptide" refers to a polypeptide that elicits a cellular and or humoral immune response, whether alone or when linked to a carrier, in the presence or absence of an adjuvant.

The term "antibody", as used herein, includes both monoclonal and polyclonal antibodies. Additionally, single polypeptide chain antigen-binding proteins, see U.S. Pat. No. 4,946,778, are included within the term "antibody".

An "individual", as used herein, refers to vertebrates, particularly members of the mammalian species and includes, but is not limited to, domestic animals, sports animals, and primates, the latter including humans.

As used herein, a "biological sample" refers to a sample of tissue or fluid isolated from an individual, including but not limited to, for example, plasma, serum, spinal fluid, lymph fluid, the external sections of the skin, respiratory, intestinal and genitourinary tracts, tears, saliva, milk, blood cells, tumors, organs, and also samples of in vitro cell culture constituents (including, but not limited to, conditioned medium resulting from the growth of cells in cell culture medium, putatively viral infected cells, recombinant cells, and cell components).

As used herein, an extracorporeal cell system (or "in vitro" cell system) refers to cells which are replicated outside of the body, i.e., cell systems not found in nature; as such, the term includes primary cultures and cell lines.

"Primary cultures", as used herein, refers to a culture of cells that is directly derived from cells or tissues from an individual, as well as cells derived by passage from these cells, but not to immortalized cells.

As used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

"Bone marrow cells", as used herein, include both primary bone marrow tissue and bone marrow cell lines from mammals, such as primates and humans, as well as precursor cells. Bone marrow cells may include, in addition to leukocytes, progenitor cells such as pluripotent stem cells. See, e.g., U.S. Pat. No. 4,714,680.

As used herein, the term "blood cell" refers to cells found either circulating in the blood, in tissue, or in bone marrow, and includes cells of the myelocytic series, the monocytic series, the megakaryocytic series, the erythrocytic series, the lymphocytic series, the plasmocytic series, and precursors thereof. The morphology by which these cells can be distinguished is discussed in Diggs, et al., THE MORPHOLOGY OF HUMAN BLOOD CELLS, Abbott Laboratories, Abbott Park, Ill. (1985). As used herein, the term "peripheral blood cell" refers to a cell found circulating in the blood, and refers generally to eosinophils, neutrophils (both band and segmented), basophils, monocytes, thrombocytes, erythrocytes, lymphocytes, plasmocytes, and precursors thereof.

As used herein, the term "leukocyte" refers to a heterogeneous group of blood cell types, having a nucleus and, as such, excludes erythrocytes and platelets. Leukocytes can be divided into two groups: polymorphonucleocytes (or [polymorphonuclear cells or granulocytes), including neutrophils, eosinophils, and basophils; and mononucleocytes (or mononuclear cells), including lymphocytes and monocytes (the latter including macrophages).

Polymorphonucleocytes contain many cytoplasmic granules and a multilobed nucleus and include the following: neutrophils, which are amoeboid in shape, phagocytic, and stain with both basic and acidic dyes; and eosinophils and basophils, which contain cytoplasmic granules that stain with acid dyes and with basic dyes, respectively.

As used herein, the term "lymphocyte" refers to mononuclear leukocytes that are agranular, spherical in shape, 6–12 $\mu$m in diameter, involved in immune responses, having a large, round, deeply staining nucleus, and possessing very little cytoplasm. In general, lymphocytes include B lymphocytes and T lymphocytes.

As used herein, "B lymphocytes" are vertebrate white blood cells which, when mature, are involved in-the production of antibody. Mature virgin B lymphocytes (i.e., those that have not encountered antigen) are characterized by the presence of the following surface markers: monomeric IgM receptors for antigen, Fc receptors for IgG; and receptors for the activated form of C3b component of complement.

Precursor B lymphocytes lack immunoglobulin products but may express other characteristic molecules that can be identified by specific monoclonal antibodies. These cells divide and undergo rapid transition to become large lymphoblasts with cytoplasmic u heavy chains but no light chains. The pre-B cell phenotype (cytoplasmic u chain$^+$, light chain$^-$, surface Ig$^-$) can be first demonstrated in lymphoblasts actively engaged in DNA synthesis. Human pre-B cells express HLA-DR molecules on their surface and may also express receptors for the C3b complement fragment. However, they lack Fc receptors for IgG and have very few C3d/EBV receptors. Precursor B lymphocytes can also be recognized by their capacity to bind peanut agglutinin.

Mature B lymphocytes may be either activated or resting. Activated B cells express several types of molecules that are not detected on resting B cells. These marker molecules are known by those of skill in the art, and include, for example, interleukin-2 (IL-2) receptors and transferrin receptors (the latter are expressed by all kinds of dividing cells). Activation of B cells provokes loss of membrane IgD, and both Fc$_\gamma$ and C3b receptors are diminished on external membranes, whereas those for C3d/EBV are not significantly affected.

After antigen or mitogen stimulation, B lymphocytes may proceed along either of 2 branches of a differentiation pathway. They can differentiate into plasma cells or they can divide and then return to a resting state as memory B cells. Memory B cells have had a loss of IgD during activation; this molecule is not resynthesized by cells entering the memory cell pool.

"Plasma cells" are terminally differentiated B lymphocytes. These cells are of ovoid shape, with an eccentric spoke-wheel nucleus, and intensely basophilic cytoplasm. When stained with fluorochrome-labeled antibodies to immunoglobulin determinants, fixed plasma cells display intense fluorescence throughout their cytoplasm. Membrane-bound immunoglobulin and DR molecules are scant, and receptors for Fc$_\gamma$, C3b, C3d, or EBV are generally undetectable.

A "plasmablast" is both morphologically and functionally between the activated lymphocyte (also called B lymphoblast) and plasma cell stages. The cells are large, with a greater nuclear:cytoplasmic ratio than plasma cells. Membrane-bound immunoglobulins and Fc$_\gamma$receptors are present.

As used herein, a "T lymphocyte" is a thymus-derived cell that may participate in a variety of cell-mediated immune responses. There are a variety of types of T lymphocytes, which are distinguishable by their function and by their cell surface markers. Methods for distinguishing the classes of T lymphocytes, which include those of the T "helper" or "inducer", T "suppressor", and "cytotoxic" T types, are known in the art. For example, monoclonal antibodies can be used to detect cell surface antigens, including the CD (cluster of differentiation) antigens. The T cell types marked by the CD antigens, and monoclonal antibodies that detect the specific antigens are shown in Table 1 below with comments.

TABLE 1

| Cell Type Marked | CD Designation | Antibody Designation |
|---|---|---|
| Gortical thymocytes[1] | CD1 | Leu 6 |
| | | OKT 6 |
| E rosette-forming cells[2] | CD2 | Leu 5 |
| | | OKT 11 |
| | | T11 |
| Mature T cells[3] | CD3 | Leu 4 |
| Helper/inducer T cells[4] | CD4 | Leu 3 |
| | | OKT 4 |
| | | T4 |
| Pan-T and -B cell subpopulation[5] | CD5 | Leu 1 |
| | | T1 |
| | | T101 |
| | | OKT1 |
| Mature T and B cell subpopulations[6] | CD6 | T12 |
| Pan-T cells, thymocytes[7] | CD7 | Leu 9 |
| | | 3Al |
| Suppressor/cytotoxic T cells[8] | CD8 | Leu2 |
| | | OHT 8 |
| | | T8 |

[1]Early T cell antigen also present on Langerhans cells, associated with beta$_2$-microglobulin not present on peripheral T cells.
[2]Pan-T cell antigen SRBC receptor on cells.
[3]Also present on T cell ALL and cutaneous T cell lymphoma.
[4]Can be further subdivided into helper and inducer subsets.
[5]B cell CLL. B cells following marrow transplant
[6]Malignant T cells.
[7]T cell leukemias.
[8]Can be further subdivided into cytotoxic and suppressor subsets.

As used herein, "large granular lymphocyte" (LGL), also called natural killer (NK) cells, are another type of lymphocyte. These cells comprise a discrete population of large lymphocytes that can be distinguished by morphologic features, for example, by characteristic azurophilic granules in their cytoplasm. In addition, LGL can be identified by methods utilizing specific monoclonal antibodies. Several monoclonal antibodies are available that detect either Fc receptors (Leu 11) or specific differentiation antigens (Leu 7, HNK-1, NKH-1, NKH-2) present on these cells. Some LGL cells also express antigens from the CD2 T cell family. Methods for functional testing are also known in the art, and are based on the ability of these nonimmune cells to kill special target cells, for example, erythroleukemia cell line K562. Methods of measuring cytotoxicity are known in the art, and include, for example, the $^{51}$Cr release assay.

As used herein, "monocytes" are large, agranular, mononuclear leukocytes that are phagocytic. As such, the term includes macrophages (i.e., monocytes found in tissue; see Table 2 below) and precursors thereof, monoblasts, and promonocytes. In humans, monocytes are approximately 10–12µm in diameter. Monocytes may be identified by their morphology. They are larger than polymorphonuclear leukocytes (granulocytes) and most lymphocytes, and have round or kidney-shaped nuclei with fine, lightly stained granules. They may be detected by staining for their non-specific esterase or alpha-naphthol esterase. Monoclonal antibodies directed at specific differentiation antigens are also available, and include, for example, Leu M3, and OKT M1. The cells of the mononuclear phagocyte system (i.e., monocytes), and their localization, are shown in Table 2 below; methods for distinguishing the cell types are discussed in Stites, et al. (eds.), BASIC & CLINICAL IMMUNOLOGY, 6th edition. Appleton and Lange, Norwalk, Conn. (1987).

TABLE 2

Cells of the Mononuclear Phagocyte System[a]

| Cells | Localization |
|---|---|
| Stem cells (committed) | Bone marrow |
| Monoblasts | Bone marrow |
| Promonocytes | Bone marrow |
| Monocytes | Bone marrow |
| Macrophages | Tissues |
| Normal state, free | |
| Histocytes | Connective tissues |
| Alveolar macrophages | Lung |
| Pleural and peritoneal macrophages | Serous cavities |
| Normal state, fixed | |
| Kupffer cells | Liver |
| Osteoclasts | Bone |
| Microglial cells | Nervous System |
| Synovial type A cells | Joints |
| Fixed tissue macrophages | Spleen, lymph nodes, bone marrow, and other tissues |
| Inflammation | |
| Exudate macrophages | Any tissue |
| Activated macrophages | Any tissue |
| Elicited macrophages | Any tissue |
| Epithelioid cells | Any tissue |
| Multinucleated giant cells (Langerhans types and foreign body type) | Any tissue |

[a]Adapted from Van Furth (ed.), MONONUCLEAR PHAGOCYTES: FUNCTIONAL ASPECTS, Martinus Nijhoff (1980).

As used herein, the term "hepatic cells" (i.e., hepatocytes, liver cells) includes any of the parenchymatous cells of the liver and their precursors, as well as cells associated with the liver, such as hepatic endothelial (or sinusoidal) cells. As such, it includes both normal and malignant liver tissue, preferably from mammalian sources, particularly nonhuman primate (e.g., chimpanzee) and human tissue.

II. Modes for Carrying out the Invention

The practice of the present invention will employ, unless otherwise indicated, conventional techniques of molecular biology, microbiology, hematology, cell and organ culture, recombinant DNA, and immunology, which are within the skill of the art. Such techniques are explained fully in the literature. See, e.g., ATCC CATALOG OF CELL LINES & HYBRIDOMAS, 6th edition, American Type Culture Collection, Rockville, Md. (1988); Stites, et al. (eds.), BASIC & CLINICAL IMMUNOLOGY, 6th edition, Appleton and Lange, Norwalk, Conn. (1987); Boggs & Winkelstein, WHITE CELL MANUAL, edition 4, F.A. Davis Co., Philadelphia, Pa. (1983); Diggs, et al., THE MORPHOLOGY OF HUMAN BLOOD CELLS, Abbott Laboratories, Abbott Park, Ill. (1985); Freshney, CULTURE OF ANIMAL CELLS: A MANUAL OF BASIC TECHNIQUE, Alan R. Liss, New York (1987); Maniatis, et al., MOLECULAR CLONING: A LABORATORY MANUAL, Cold Spring Harbor Laboratory Press, Cold Spring Harbor, N.Y. (1982); Sambrook, et al., MOLECULAR CLONING: A LABORATORY MANUAL, Cold Spring Harbor Laboratory Press, Cold Spring Harbor, N.Y. (1989); Glover (ed.), DNA CLONING, VOLUMES I AND II (1985); Clemens, et al. (eds.), LYMPHOEKINES AND INTERFERONS: A PRACTICAL APPROACH, IRL Press, Washington, D.C. (1987); Klaus (ed.), LYMPHOCYTES: A PRACTICAL APPROACH, IRL Press, Washington, D.C. (1987); Mahy (ed.), VIROLOGY: A PRACTICAL APPROACH, IRL Press, Washington, D.C. (1985); Gait (ed.), OLIGONUCLEOTIDE SYNTHESIS (1984); Hames, et al. (eds.), NUCLEIC ACID HYBRIDIZATION, (1984); IM-MOBILIZED CELLS AND ENZYMES, RL Press, Washington, D.C. (1986); B. Perbal, A PRACTCAL GUIDE TO MOLECULAR CLONING (1984); the series METHODS IN ENZYMOLOGY, Academic Press, London, in particular, volumes 154 and 155; Miller, et al. (eds.), GENE TRANSFER VECTORS FOR MALLIAN CELLS, Cold Spring Harbor Press, Cold Spring Harbor, N.Y. (1987); Mayer & Walker (eds.), IMMUNOCHCAL METHODS IN CELL AND MOLECULAR BIOLOGY, Academic Press, London (1987); Scopes, PROTEIN PURIFICATION: PRINCIPLES AND PRACTICE, second edition, Springer-Verlag, New York (1987); and Weir & Blackwell (eds.), HANDBOOK OF EXPERIMNAL IMMUNOLOGY, volumes I–IV (1986).

A. Candidate cell Systems for HCV-Infection

A wide variety of candidates for HCV-infected cell systems exist. Candidate cell systems are preferably mammal in origin and, more preferably primate, particularly human. Extracoiporeal cell systems must be susceptible to HCV infection and may be primary cultures or established cell lines. Many cell types can be considered potential candidates, including, but not limited to, hepatocytes; macrophages, preferably Kupffer macrophages; and B lymphocytes. Preferred cell types or lines can be identified through screening for HCV infection and growth in culture using the techniques described herein (e.g., HCV/cPCR, as described below) and routine skill in the art.

Additionally, as described below in Section II.B., a wide variety of cells can be transfected with specified receptors, i.e., mannose and/or asialoglycoprotein receptors, and then infected with HCV.

A general class of preferred cell types for HCV infection replication is mononucleocytes, in particular macrophages and B lymphocytes. Mononucleocyte cell systems that may be infected with HCV include primary cultures and cell lines derived from primary cultures of mononucleocytes. Methods to obtain immoxtalized cell lines of types of mononucleocytes are known in the art. For example, methods for growing and immortalizing B cells, T cells, and macrophages in culture are described in Klaus (ed.), LYMPHOCYTES: A PRACTICAL APPROACH, IRL Press, Washington, D.C. (1987); Clemens, et al., LYMPHOKINES AND INTERFERONS: A PRACTICAL APPROACH, IRL Press, Washington, D.C. (1987); and Freshney, CULTURE OF ANIMAL CELLS: A MANUAL OF BASIC TECHNIQUE, Alan R. Liss, New York (1987).

More specifically and preferably, B lymphocyte lines are often inmortalized by infection with Epstein-Barr virus (EBV). This may be accomplished by incubating mononucleocytes from infected cells with the supernatant from an EBV-infected cell line that is a chronic shedder of EBV. Preferred EBV lines are those from chimpanzees.

Mononucleocytes may be derived from known established cell lines, many of which are available from the American Type Culture Collection (ATCC) and include, for example, EBV-transformed B cell derived lines such as B95-8, DAKIKI, LTR228, Mo-B, SC-1, WIL2-NS; B cell lines such as Ia2, BL-3, UC 729-6, Namalwa, U-937, Ramos (RA-1), $BCL_1$ clone $5B_1b$, MC/CAR, IA2, YB2/0, CA3-F4, SHM-D33, CW13.20-3B3, BC9-E%, WM-115, WM 266-4, WEHI-231, WEHI-279, NFS-1.0 C-1; monocyte lines such as THP-1, WEHI-274.1; mouse lymphoma lines such as 2pk-3; pro-B lymphoblasts such as NFS-70 C-10; pre-B lymphoblasts such as NFS-25 C-3; T-cell derived lines such as CTLL-2, HuT 102, D10.G4.1, LBRM-33 clone 4A2, HuT78, $Cl.Ly1^{+}2^{-}/9$, UCD-MLA-144, 6T-CEM 20, 6T-CEM, CCRF-CEM, H9/HTLV-IIIB, CCRF-SB, CCRF-HSB-2, CEM-CM3, Mo, MOLT-3, MOLT-4, BW5147.3, BW5147.G.1.4, C1498, RAW8. 1, CTLL-2, and $BW5147.G.1.4.OUA^R.1$. Additional human leukemia cell lines of interest include K562 and ARH-77. Conditions for the in vitro culture of these cells is described in ATCC CATALOG OF CELL LINES AND HYBRIDOMAS, 6th edition, American Type Culture Collection, Rockville, Md. (1988).

Preferred monocyte cell systems are macrophages selected from the group consisting of histocytes, alveolar macrophages, pleural macrophages, peritoneal macrophages, Kupffer cells, osteoclasts, microglial cells, synovial type A cells, fixed tissue macrophages, exudate macrophages, activated macrophages, elicited macrophages, epitheloid cells, and multinucleated giant cells. In general, normal mature macrophages do not proliferate; however, replicating precursor cells of macrophages may be cultured by techniques known in the art, see, for example, Freshney, CULTURE OF ANIMAL CELLS: A MANUAL OF BASIC TECHNIQUE, Alan R. Liss, New York (1987), at pages 284–287. Most preferred macrophages are Kupffer cells, which are found in the liver.

The growth of mononucleocytes in culture is often assisted by the presence of stimulatory protein factors (also called cytokines) in the culture medium; these factors are usually produced by a cell of another type. A supply of the cytokines may be provided in conditioned medium, i.e., cell culture supernatant from cells that produce the desired factors. Alternatively, cytokines may also be provided by feeder cells. The requirement may also be met by the provision of the purified cytokines.

Cytokines include interleukin 1-alpha and beta (also called lymphocyte activating factor, epidermal cell derived thymocyte activating factor, and hemopoietin H1) derived from multiple cell types, including monocytes, lymphocytes, and keratinocytes. Interleukin 1-alpha and beta have multiple actions, including stimulating interleukin 2 production and hematopoietic activity. Interleukin 2 (also called T cell growth factor), is derived from T lymphocytes and stimulates T and B lymphocyte proliferation and differentiation, macrophage activation, and natural killer cell activation. Interleukin 3 (also called Multi-CSF) is derived from T lymphocytes and has a pluripotent effect on growth and differentiation as well as stimulating mast cell growth. Interleukin 4 (also called B-cell growth factor I) is derived from T lymphocytes and stimulates T and B lymphocyte proliferation and differentiation. Interleukin 5 (also called B cell growth factor II) is derived from T lymphocytes and stimulates eosinophil differentiation (and, in the mouse system, acts as a B cell growth factor).

Also included are the following stimulator protein factors. Low molecular weight B cell growth factor is derived from T lymphocytes and stimulates B lymphocyte proliferation. B cell stimulatory factor 2 (also called interferon beta-2) is derived from T lymphocytes and stimulates B lymphocyte differentiation. Interferon-gamma (also called immune interferon) is produced by T lymphocytes and activates macrophages. Granulocyte colony stimulating factor (G-CSF) is derived from a number of cell types and stimulates the growth and differentiation of granulocytes. Macrophage colony stimulating factor (M-CSF 1) is derived from a number of cell types and stimulates the growth and differentiation of monocytes/macrophages. Granulocyte macrophage colony stimulating factor (GM-CSF) is derived from a number of cell types and stimulates the growth and differentiation of monocytes/granulocytes.

Bone marrow cells may also be used as extracorporeal cell systems for HCV infection. Primary bone marrow cells may include, in addition to leukocytes, progenitor cells such as pluripotent stem cells. Methods of culturing primary bone marrow cells in vitro are known, In addition, bone marrow cell lines, such as IM-9, KG-1, and KG-1a are available, see, e.g., ATCC CATALOG OF CELL LINS & HYBRIDOMAS, 6th edition, American Type Culture Collection, Rockville, Md., at 361.

Other types of cell systems that may be used for propagation of HCV are derived, for example, from organ tissues. A preferred source of such tissue is the liver. Primary hepatocytes can be cultured and then infected with HCV or, alternatively, the hepatocyte cultures can be derived from the livers of infected individuals (e.g., humans or chimpanzees). The latter case is an example of a cell system that is infected in vivo and passaged in vitro.

In addition, various immortalization methods can be used to obtain cell lines derived from primary organ tissue. For example, the primary cell cultures may be fused to a variety of cells to form hybridomas and to maintain stability. Also, cultures may be infected with transforming viruses (e.g., Epstein-Barr virus, EBV) or transfected with transforming genes in order to create permanent or semipermanent cell lines. In addition, primary cells in culture may be fused to established cell lines. Methods for cell fusion are known in the art, and include, for example, the use of fusion agents, such as polyethylene glycol.

Among the preferred organ tissue cell lines are those of hepatic origin. Established hepatic cell lines include Hep G2, Hep 3B, Chang liver, CLCL, PLC/PRF/5 (Alexander), SK-HEP-1, and WRL 68, see, e.g., ATCC CATALOG OF CELL LINES & HYBRIDOMAS, 6th edition, American Type Culture Collection, Rockville, Md., at 362. Particularly preferred hepatocytes are human hepatocellular carcinoma (HCC) cell lines, such as Hep G2. Other suitable cells or cell lines for culturing HCV include hepatocytes or hepatocyte cell lines such as HUH7.

B. Culture of HCV in Cell Lines Expressing Mannose and/or Asialoglycoprotein Receptors The tissue specificity of HCV, in combination with the observation that HCV envelope glycoproteins are mannose-terminated, suggests that the virus employs the mannose receptor or the asialoglycoprotein receptor (ASGR) in order to gain entry into host cells. Mannose receptors are found on macrophages and hepatic endothelial sinusoidal cells, whereas the ASGR is found on parenchymal hepatocytes. Thus, it should be possible to culture HCV by employing host cells that express one or both of these receptors.

One may either employ primary cell cultures that naturally express the receptor, using conditions under which the receptor is maintained, or one may transfect another cell line such as HeLa, CHO, COS, and the like, with a vector providing for expression of the receptor. Cloning of the mannose receptor and its transfection and expression in fibroblasts has been demonstrated by Taylor, et al., *J. Biol. Chem.* 265:12156–62 (1990). Cloning and sequencing of the ASGR was described by Drickamer, et al., *J. Biol. Chem.* 259:770–78 (1984) and Speiss, et al., *Proc. Natl. Acad. Sci. USA* 82:6465–69 (1985); transfection and expression of functional ASGR in rat HTC cells was described by McPhaul, et al., *Proc. Natl. Acad. Sci. USA* 83:8863–67 (1986) and McPhaul, et al., *Mol. Cell Biol.* 7:1841–47 (1987).

Thus, it is possible to transfect one or both receptors into suitable cell lines, such as CHO, COS, HeLa, and the like, and to use the resulting cells as hosts for propagation of HCV in culture. Serial passaging of HCV in such cultures should result in development of attenuated strains suitable for use as live vaccines. It is presently preferred to employ an immortlized cell line transfected with one or both recombinant receptors.

C. Detection and Isolation of HCV-Infected Cells From an Individual

HCV-infected cells in biological samples can be screened for the presence of HCV polypeptides or HCV polynucleotides, see generally EPO Publ. No. 318,216 (published May 31, 1989); EPO Publ. No. 388,232 (published Sep. 19, 1990). For example, the biological samples can be blood samples, from which HCV-infected cells and/or cells replicating HCV are isolated and partially purified utilizing techniques known in the art, for example, by sedimentation through Ficoll-Paque (Phannacia Corp.) solutions.

Identification of infected cell types may be accomplished by utilizing techniques known in the art, for blood cell types see, e.g., Klaus (ed.), LYMPHOCYTES: A PRACTICAL APPROACH, ERL Press, Washington, D.C. (1987). These procedures may use monoclonal antibodies directed toward specific cell types, such as blood cell types. For example, monoclonal antibodies directed to surface epitopes on various lymphocytes and monocytes/macrophages are known in the art and commercially available. The monoclonal antibodies may be affixed to solid substrates, e.g., plates with wells or magnetic beads. Thus, HCV-infected cells may be isolated and identified by immunologic binding to specific cell surface antigens. Alternatively, sorting techniques, which rely upon cell sorter instruments, may be used. The selection may be either positive or negative to enrich and/or select the desired cells.

The screening technique used to detect viral material must be sufficiently sensitive to detect very limited amounts of viral polypeptides or polynucleotides. It is anticipated that various strains or isolates of HCV will be present in the infected cells of various individuals. Therefore detection methods should be directed to constant epitopes or genomic sequences of HCV.

The presence of virions may be detected using immunoassays having, for example, antibodies directed against virion polypeptide(s). Methods of making anti-HCV antibodies are described in EPO Publ. No. 318,216 (published May 31, 1989); EPO PubI. No. 388,232 (published Sep. 19, 1990). Methods for immunoassays, as well as methods for signal enhancement, are known in the art.

The HCV genomic material, and replicative intermediates thereof, may also be detected by nucleic acid hybridization. In a preferred embodiment, detection of viral material is accomplished by identifying replicative intermediates of the viral genome in preparations containing HCV-infected cells. Preferably, the employed hybridization assay will involve amplification techniques. Such techniques are known in the art.

For example, the "Bio-Bridge" system (Enzo Biochemical Corp.) uses terminal deoxynucleotide transferase to add unmodified 3'-poly-dT-tails to a DNA probe. The poly dT-tailed probe is hybridized to the target nucleotide sequence, and then to a biotin-modified poly-A. PCT Pub. No. WO 84/03520 (published Sep. 13, 1984) describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPO Pub. No. 204,510 (published Dec. 10, 1986) describes a DNA hybridization assay in which analyte DNA is contacted with a probe that has a tail, such as a poly-dT tail, an amplifier strand that has a sequence that hybridizes to the tail of the probe, such as a poly-A sequence, and that is capable of binding a plurality of labeled strands.

A preferred technique may first involve amplification of the target HCV sequences in sera until the amplified sequences are at a detectable level. This may be accomplished, for example, by PCR, as described in Saiki, et al., Nature 324:163 (1986); U.S. Pat. No. 4,683,195; and U.S. Pat. No. 4,683,202. The amplified sequence(s) may then be detected using a hybridization assay which is described in commonly owned EPO Publ. No. 317,077 (published May 24, 1989). These hybridization assays, which should detect sequences at the level of $10^6$/ml, utilize nucleic acid multimers which bind to single-stranded analyte nucleic acid, and which also bind to a multiplicity of single-stranded labeled oligonucleotides. A suitable solution phase sandwich assay may be used with labeled polynucleotide probes, and methods for the preparation of probes is described in EPO Pub. No. 225,807 (published Jun. 16, 1987).

One method for detecting HCV genomic sequences is described in the Examples. This method is based on an HCV/cPCR method described in commonly owned U.S. Ser. No. 07/355,961. The method utilizes primers and probes based upon a family of cDNA replicas of portions of the HCV genome. The first step in the method is the synthesis of a cDNA to either the HCV genome or its replicative intermediate, using reverse transcriptase. If replicative intermediates are to be detected, the primer is complementary to only the minus strand of HCV RNA (i.e, the strand which is the replicative intermediate). After synthesis of the HCV cDNA, and prior to amplification, the RNA in the sample is degraded by techniques known in the art, for example, by alkali denaturation, or by treatment with an RNA specific RNase.

Utilizing the HCV/cPCR method described above to screen fractions of a partially purified composition of mononucleocytes derived from peripheral blood of HCV-infected individuals and separated from erythrocytes and polymorphonucleocytes on Ficoll-Paque (Pharmacia Corp.), replicative intermediates of the HCV genome were detected in the mononucdeocyte composition (see Examples below). This method can be used to identify various cell types that can be employed for HCV cell cultures.

D. Methods for Producing HCV-Infected Extracoiporeal Cell Systems

In addition to HCV-infected extracorporeal cell systems, the present invention relates to methods for producing an HCV-infected extracorporeal cell system comprising: (a) providing an extracorporeal cell system capable of being infected by HCV; (b) providing a source of infective HCV; and (c) infecting the cell line of (a) with the infective HCV of (b) under conditions that allow cell infection. Also included are the HCV-infected cell systems produced according to these methods.

HCV-infection of an extracorporeal cell system capable of being infected by HCV, i.e., a susceptible cell system, may be accomplished by any one of several techniques using a variety of HCV source materials. Some of these techniques are discussed below. Generally, virus particles adsorb to cultured cells at physiological temperatures. The virus penetrates, uncoats, replicates its nucleic acid in the nucleus or cytoplasm, and, after transcription and translation, assembles progeny virions that egress either by cell lysis or budding. The number of progeny virus particles released from one cell is referred to as the burst size. Virus can be titrated, for example, by adsorbing serial tenfold dilutions to cells and counting the resultant plaques after appropriate incubation at the permissive temperature.

Viral infection of HCV-susceptible cell systems may be accomplished by co-cultivation of the susceptible cell systems and HCV-infected cells. The HCV-infected cells may be from a primary culture or from a cell line. Usually the HCV-infected cells and the susceptible cell system are incubated together in approximately equal numbers in an appropriate cell culture medium. The medium may contain Polybrene (Abbott Laboratories), or a functionally similar substance, in an appropriate concentration. The incubation is of sufficient time and at the appropriate temperature to allow the newly replicated virus from the HCV-infected cells to allow attachment and uptake by the susceptible cell system.

Additionally, infection of HCV-susceptible cell systems may also be accomplished using concentrated supernatant culture fluids harvested from cultures of cells replicating HCV. Generally the susceptible cell systems are pretreated with an appropriate concentration of Polybrene (Abbott Laboratories) (or a functionally similar substance), and then exposed to concentrated culture fluids harvested from shortterm primary cultures of HCV infected cells derived from infected individuals.

Another option is to directly infect HCV-susceptible cell systems with virus isolated from HCV-containing biological samples. Suitable methods for the isolation of viruses, particularly RNA containing viruses, and more particularly Togaviruses and Flaviviruses are known in the art, for example, see Mahy (ed.), VIROLOGY: A PRACTICAL APPROACH, IRL Press, Washington, D.C. (1985).

Another method for preparing HCV-infected cells in vitro may be by the fusion of HCV-infected cells with HCV-susceptible cells. Methods for fusing somatic cells are known in the art, as are methods for the selection of fused cells. For example, fusion may be catalyzed by the presence of chemicals, e.g., polyethylene glycol. The susceptible cell may carry a marker that prevents its growth in the selection media, e.g., the cells may be phenotypically negative for thymidine kinase. Selection is then in media requiring the marker, e.g., HAT medium for thymidine kinase. This method is particularly suitable if the HCV-infected cells isolated from the infected individual do not replicate in vitro.

Yet another method of preparing an HCV-infected cell system is by immortaization of infected cells isolated from an individual with hepatitis C. Generally, cells are isolated and then grown in primary culture. Immortalization may be accomplished by growing and passaging the cells through the cell crisis period, at which point the majority of cultured cells die; the resulting cells are immortal.

The results presented herein indicate that, viral replication is detected in HCV-infected cells not actively replicating. Therefore, the cells should be cultured in a medium that minimizes cell growth and maximizes the expression of cellular functions required for HCV infection and replication. In a preferred embodiment wherein hepatocytes are used as the susceptible cell system, the preferred medium is a serum-free medium.

The present invention also relates to methods for producing an HCV-infected extracorporeal cell systems also comprise: (a) providing an extracorporeal cell system capable of being infected by HCV;(b) providing an RNA reagent comprising full-length HCV RNA; and (c) transfecting the cell system of step (a) with the RNA reagent of step (b) under conditions that allow cell transfection. In a preferred embodiment, the RNA reagent of step (b) also contains a 5'-truncated HCV RNA for co-transfection. Preferably the co-transfected 5'-truncated HCV RNA is a full-length HCV RNA lacking from about 40 to about 200, more preferably from about 80 to about 160, even more preferably about 144 nucleotides at the 5' end.

Thus, one may obtain viral production by transfecting the cells with isolated viral polynucleotides. It is known that Togavirus and Flavivirus RNAs are infectious in a variety of vertebrate cell lines (Pfefferkorn and Shapiro (1974)), and in a mosquito cell line Foeleg (1969)).

Methods for transfecting tissue culture cells with RNA duplexes, positive stranded RNAs, and DNAs (including cDNAs) are known in the art, and include, for example, techniques which use electroporation, and precipitation with DEAE-Dextran or calcium phosphate. An abundant source of HCV RNA can be obtained by performing in vitro transcription of an HCV cDNA corresponding to the complete genome. Transfection with this material, or with cloned HCV cDNA should result in viral replication and the in vitro propagation of the virus. Co-transfection with the full length and 5'-truncated HCV RNAs does result in viral replication and the in vitro propagation of the virus.

Mammalian transformations (transfections) by direct uptake may be conducted using the calcium phosphate precipitation method of Graham and Van der Eb (1978), or the various known modifications thereof. Other methods for the introduction of recombinant polynucleotides into cells, particularly into mammalian cells, which are known in the art include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

In addition to cultured cells, animal model systems may be used for viral replication; animal systems in which flaviviruses replicate are known to those of skill in the art (see, for example, the review by Monath (1986)). Thus, HCV replication may occur not only in chimpanzees, but also in, for example, marmosets and suckling mice.

HCV infection and replication in the HCV-infected cell systems constructed as described above may be detected by a variety of assays. For example, viral assays may depend upon the cytopathic or transforming characteristics of the virus.

Cytopathic viruses may be assayed by their antimetabolic effects in microtitration plates or by the formation of characteristic plaques in monolayers of the appropriate susceptible host cell. A viral suspension can be serially diluted and added to monolayer culture plates. The number of plaques forming at the limiting dilution is taken as equivalent to the number of infectious particles in the supernatant medium, allowing the concentration of virus in the initial sample to be calculated. Characterization of the virus may be performed with specific antisera measuring the cytopathic effect of the virus, by immunoassay, or by the HCV/cPCR assay for HCV RNA as described above. Transforming viruses may be assayed, for example, by the selective growth of transformed clones in suspension or by looking for transformation foci in monolayer cultures.

In the event that the virus of interest does not exhibit either a detectable cytopathic or transforming effect, it may be detected in the infected cell preparation or infected cell lysate by a number of techniques, including, for example, immunoassay using a labeled antibody(s) specific for the virus; immunoassay of polypeptides labeled during replication using HCV antibodies; and the detection of viral nucleic acids, for example, an enriched population of minus strands complementary to viral plus strands or viral nucleic acids labelled during an in vitro viral synthesis period.

E. Vaccines from HCV-Infected Extracoiporeal Cell Systems

The present invention relates to HCV-infected extracorporeal cell systems, which have applications in vaccine compositions. Such vaccines comprise, for example, an immunologically effective amount of an HCV-infected extracorporeal cell system product consisting of HCV polypeptide-containig fractions of cell lysates, whole cells, and cell culture supernatants admixed with a pharmaceutically acceptable carrier, preferably further comprising an adjuvant.

Any cell product that is immunologically effective, i.e, contaning HCV antigen can be used. As such, it includes whole cells, HCV polypeptide-containing cell fractions of cell lysates, as well as supernatants from the infected cell systems. The latter form may be preferred when the selected cell system is a malignant cell line. Cell lysates may be prepared by methods known in the art. Such methods include, but are not limited to, physical disruption, chemical lysis, and the like. Preferred cell systems include, but are not limited to, hepatocytes; macrophages, more preferably Kupffer cells; and B lymphocytes.

Pharmaceutically acceptable carriers include any carrier that does not itself induce the production of antibodies harmful to the individual receiving the vaccine. Suitable carriers are typically large, slowly metabolized macromolecules such as proteins, polysaccharides, polymeric amino acids, amino acid copolymers; and inactive virus particles. Such carriers are well known to those of ordinary skill in the art.

Preferred adjuvants to enhance effectiveness of the vaccine include, but are not limited to: aluminum hydroxide (alum), N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-aianine-2-(1'-2'-ipalmitoyl-sn-glycero-3-huydroxyphosphoryloxy)-ethylamine (TP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Additionally, adjuvants such as Stimulon (Cambridge Bioscience, Worcester, Mass.) may be used.

Furthermore, the present vaccines may contain pharmaceutically acceptable excipients compatible with the HCV-infected cell system product, such as water, saline, glycerol, ethanol, etc. Additionally, auxiliary substances, such as wetting or emulsifying agents, pH buffering substances, and the like, may be present.

Typically, vaccines are prepared as injectables, either as liquid solutions or suspensions; solid forms suitable for solution in, or suspension in, liquid prior to injection may also be prepared. The preparation also may be emulsified or encapsulated in liposomes.

The vaccine comprises an immunologically effective amount of the HCV-infected cell system lysate. By "immunologically effective amount", it is meant that amount necessary to be prophylactically and/or therapeutically effective against hepatitis C. This amount varies depending upon the health and physical condition of the individual to be treated, the capacity of the individual's immune system to synthesize antibodies, the degree of protection desired, the formulation of the vaccine, the treating physician's assessment of the medical situation, and other relevant factors.

The vaccines are conventionally administered parenterally, by injection, for example, either subcutaneously or intramuscularly. Additional formulations suitable for other modes of administration include oral formulations and suppositories. Dosage treatment may be a single dose schedule or a multiple dose schedule. The vaccine may be administered in conjunction with other immunoregulatory agents.

F. Immunoassays Using Cell Products From Extracorporeal HCV-Infected Cell Systems A further aspect of the present invention is an immunoassay for detecting antibodies directed against an HCV antigen comprising: (a) incubating a biological sample suspected of containing anti-HCV antibodies with a cell product of an HCV-infected extracorporeal cell system, wherein the cell product contains HCV antigens that react immunologically with HCV antibodies, under conditions that allow the formation of an antibody-antigen complex; and (b) detecting the antibody-antigen complex. Preferred cell systems include hepatocytes; macrophages, more preferably Lupffer cells; and B lymphocytes.

Cell products from the HCV-infected extracorporeal cell systems that react immunologically with HCV antibodies are useful in immunoassays to detect presence of HCV antibodies in biological samples, such as blood serum. The HCV-infected cell system products from whole cells, cell lysates, or supernatant form can consist of, for example, virus particles or viral polypeptides that serve as HCV antigens. For example, the cell system product containing HCV antigens may consist of a combination of viral epitopes derived from the same or from different viral polypeptides. Additionally, one or more viral antigens may be isolated from the HCV-infected cell or from isolated HCV.

Design and protocol of the immunoassays is subject to a great deal of variation, and a variety of these are known in the art. Protocols may be based, for example, upon competition, direct reaction, or sandwich type assays. In one preferred embodiment, whole cells or an HCV polypeptide-containing fraction can be affixed to a solid support. "Solid support" refers to any surface that is transferable from solution to solution or that forms a structure for conducting an antigen-antibody assay, and includes beads, membranes, microtiter plates, strings, plastic strips, or any surface onto which antigen may be immobilized. Immunoprecipitation may also be used.

Most assays involve the use of labeled antibody for detection; the labels may be, for example, fluorescent, chemiluminescent, radioactive, dye molecules, or enzymatic tags. Assays that amplify signals from a probe are also known in the art; examples of which are assays utilizing biotin and avidin, and enzyme-labeled and mediated immunoassays, such as enzyme-linked immunosorbent assays (ELISAs). In an ELISA, the biological sample to be tested for anti-HCV antibodies is added to a solid support having HCV antigen affixed thereto, and the formation of HCV antibody-HCV antigen complexes is detected by measuring enzyme activity bound to the solid support when a specific substrate is added, and determining product formation or substrate utilization colorimetrically. The enzyme activity bound is a direct function of the amount of antibody bound.

Another suitable immunoassay may utilize gel electrophoresis of lysates from HCV-infected cell systems followed by a Western Blot or RMBA™ type with the biological sample to be tested for anti-HCV antibodies. The formation of HCV antibody-HCV antigen complexes is detected using techniques known in the art Additionally, competition assays with labeled anti-HCV monoclonal or polyclonal antibodies may be employed.

Kits suitable for immunodiagnosis and containing the appropriate labeled reagents can be constructed by packaging the appropriate materials, including the HCV-infected cell system products, in suitable containers, along with the remaining reagents and materials required for the conduct of the assay, as well as a suitable set of assay instructions.

G. Use of Extracorporeal Cell Systems in Screening Putative HCV Antiviral Agents The HCV-infected extracorporeal cell systems described herein, which are capable of HCV infection and replication, may be used to screen for antiviral agents that inhibit HCV infection and/or replication. Antiviral agents include any protein, polysaccharide, lipid, polynucleotide, or other organic composition or substance that prevents viral infection or replication. As such, included within the category of antiviral agents are antibodies that block viral infection (neutralizing antibodies) or those that mediate antibody-dependent cellular cytotoxicity (ADCC). Preferred antiviral agents preferentially allow cell growth and multiplication while inhibiting viral infection and/or replication. Methods for screening putative antiviral agents that inhibit HCV infection and comprise: (a) providing a composition comprised of a putative antiviral agent; (b) providing an extracorporeal cell system capable of being infected by HCV; (c) providing a biological sample containing infective HCV; (d) incubating the compositions of (a) and (c) with the cell system of (b) under conditions that would, in the absence of (a), allow infection of HCV in the cell system; and (e) detecting inhibition of viral infection after incubation. Preferred cell systems include, but are not limited to, those delineated above.

Additionally, putative antiviral agents that inhibit HCV replication in HCV-infected cell systems can be screened using present methods that comprise: (a) providing a putative antiviral agent; (b) providing a HCV-infected extracorporeal cell system; (c) incubating the compositions of (a) and (b) under conditions that would, in the absence of (a), allow replication of HCV in the cell line; and (d) detecting inhibition of viral replication after incubation.

Generally, the putative antiviral agents are tested at a variety of concentrations for their effect on preventing viral infection and/or replication in a HCV-infected cell system of the present invention. Likely antiviral agents then can be tested in an animal model system for an inhibition of infectivity or of viral pathogenicity as well as for low levels of toxicity.

III. Examples

The following examples illustrate detection of HCV RNA and HCV RNA minus strands in mononucleocytes from individuals infected with hepatitis C. Propagation of HCV in a hepatocellular carcinoma (HCC) cell line, Hep G2, is also presented.

These examples are only illustrative and are not to be interpreted as limiting the present invention. Although the present invention has been described above by way of illustration, it is not limited to these examples, and its scope is to be defined by the appended claims and the equivalents thereof. Many variations within the scope of the present invention will be obvious to one of ordinary skill in the art.

A. Detection of HCV RNA in Mononucleocytes From HCV-Infected Individuals

The detection of HCV RNA in mononucleocytes from blood of HCV-infected individuals was accomplished using the HCV/cPCR assay described in U.S. Ser. No. 071355, 961, which is owned by the present assignee.

Blood obtained from 5 individuals with chronic hepatitis C and that tested positive for anti-HCV antibodies using an HCV-C100 antigen immunoassay, and from 5 control individuals (reportedly free of hepatitis C and that was negative in the immunoassay) was examined for the presence of HCV RNA in the mononucleocyte fraction. A mononucleocyte fraction from the samples was obtained by sedimentation through Ficoll-Paque (Pharmacia Corp.), using the manufacturer's directions.

The HCV/cPCR assay used in these studies was performed utilizing the following methods for the preparation of RNA, the reverse transcription of the RNA into cDNA, the amplification of specific segments of the cDNA by PCR, and the analysis of the PCR products.

Total RNA was isolated from the mononucleocyte fraction. The cDNA used as a template for the PCR reaction was prepared utilizing the designated samples for preparation of the corresponding cDNAs. Each RNA sample (corresponding to cells in 10 microliters of blood) was incubated in a 25 microliter reaction containing 1 micromolar of each primer, 1 millimolar of each deoxyribonucleotide triphosphate (dNTP), 50 millimolar Tris-HCL, pH 8.3, 5 millimolar $MgCl_2$, 5 millimolar dithiothreitol (DTT), 73 millimolar KCl, 40 units of RNase inhibitor (RNASIN), and 5 units of AMV reverse transcriptase. The incubation was for 60 minutes at 37° C.

Following cDNA synthesis, the reactions were diluted with 50 microliters of deionized water (DIW), boiled for 10 minutes, and cooled on ice.

Amplification of a segment of the HCV cDNA was performed utilizing two synthetic 16-mer oligonucleotide primers whose sequences were derived from HCV cDNA clones 36 (anti-sense or minus) and 37b (sense or plus), see, e.g., EPO Pub. No. 318,216 (published May 31, 1989), which is owned by the present assignee. The primers were used at a final concentration of 1 micromolar each. In order to amplify the segment of HCV cDNA flanked by the primers, the cDNA samples were incubated with 0.1 microgram of RNAse A and the PCR reactants of the Perkin Elmer Cetus PCR kit (N801-0043 or N801-0055) according to the manufacturer's instructions.

The PCR reaction was performed for either 30 cycles or 60 cycles in a Perkin Elmer Cetus DNA thermal cycler. Each cycle consisted of a 1 minute denaturation step at 94° C., an annealing step of 2 minutes at 37° C., and an extension step of 3 minutes at 72° C. However, the extension step in the final cycle (30 or 60) was 7 minutes rather than 3 minutes. After amplification, the samples were extracted with an equal volume of phenol: chloroform (1:1), followed by extraction with an equal volume of chloroform, and then the samples were precipitated with ethanol containing 0.2 M sodium acetate.

The cPCR products were analyzed as follows. The products were subjected to electrophoresis on 1.8% alkaline agarose gels according to Murakawa, et al., DNA 7:287 (1988), and transferred onto Zeta Probe paper BioRad Corp.) by blotting gels overnight in 0.4 M NaOH. The blots were neutralized in 2 ×SSC (1 ×SSC contains 0.15 M NaCl, 0.015 M sodium citrate), prehybridized in 0.3 M NaCl, 15 mM sodium phosphage buffer, pH 6.8, 15 mM EDTA, 1.0% SDS, 0.5% nonfat milk (Carnation Co.), and 0.5 mg/ml sonicated denatured salmon sperm DNA. The blots to be analyzed for HCV cDNA fragments were hybridized to a $^{32}P$-labeled probe generated by nick translation of the HCV cDNA insert sequence in clone 35, see EPO Pub. No. 318,216 (published May 31, 1989), which is owned by the present assignee.

After hybridization, the blots were washed in 0.1 ×SSC (1 ×SSC contains 0.15M NaCl, 0.01M Na citrate) at 65° C., dried, and autoradiographed. The expected product size is 586 nucleotides in length; products which hybridized with the probe and migrated in the gels in this size range were scored as positive for viral RNA.

As a control, cPCR primers designed to amplify alpha-1 aptitrypsin MRNA was employed to verify the presence of RNA in each sample analyzed. The coding region of the alpha-1 anti-trypsin gene is described in Rosenberg, et al., Nature 312:7 (1984). Synthetic 16-mer oligonucleotide primers designed to amplify a 365 nucleotide fragment of the coding region of the alpha-1 antitrypsin gene were derived from nucleotides 22–37 (sense or plus) and nucleotides 372–387 (antisense or minus). The PCR products were detected using a $^{32}P$ nick-translated probe that lies between, and not including, the cDNA/PCR primer sequences.

Due to the extreme sensitivity of the PCR reaction, all samples were run a minimum of three times. All false positive signals were eliminated when the following precautions were taken: (1) eliminating aerosols by using screw-capped tubes with rubber O-ring seals; (2) pipetting with Ranin Microman positive displacement pipetters with disposable pistons/capillaries; and (3) selecting the oligonucleotide sequences for the cDNA and PCR primers from two noncontiguous cDNA clones.

The results showed that mononucleocytes from 5 of the 5 HCV anti-C100 antibody positive samples were positive for HCV RNA in the HCV/cPCR assay. All of the controls were negative in the same assay.

B. Detection of HCV RNA Minus Strands in Mononucleocytes From HCV-Infected Individuals The detection of HCV RNA minus strands in mononucleocytes from blood of HCV-infected individuals was accomplished using the HCV/cPCR assay as described above in Section III.A., except that the cDNA was synthesized using either the 16-mer primer from clone 36 (i.e., primer 36/16A), described in Section III.A., to prime the plus strand of HCV RNA or the complement of the 16-mer (i.e., primer 36/16B) to prime the minus strand.

In order to carry out the subsequent PCR reaction, the cDNA reaction mixture was boiled and treated with RNase prior to the addition of the second primer.

The results of the HCV/cPCR assay showed that 5 of the 5 HCV anti-C100 antibody positive samples were positive for HCV minus strands; of these five samples, two showed high levels of HCV RNA minus strands. All 5 of these samples were about equally positive for the plus strands of HCV RNA Of the five control samples, all were negative for both plus and minus strands of HCV RNA. As an additional control, plasma samples from three of the HCV-infected individuals were also analyzed. The signal obtained from the plus strands was at least 5 to 10 times stronger than was the signal for the minus strands. Thus, the plasma samples were strongly positive for the plus strands, and only weakly positive to negative for the minus strands.

In HCV, which is Flavi-like, the viral genome is positive-stranded RNA. The discovery of the great enrichment of minus strands of HCV RNA in mononucleocytes, relative to that in plasma, suggests that replicative intermediates of the viral genome are present in these cells.

C. Propagation of HCV in a Hepatocellular Carcinoma (HCC) Cell Line

Infectious plasma containing HCV was used to infect a continuously grown hepatic cell line, Hep G2 (ATCC No. HB 8065). In order to propagate HCV, the Hep G2 cells were cultured in serum-free medium in order to minimize cell growth and maximize expression of cellular functions required for viral infection and replication.

More specifically, the procedure was the following. Hep G2 cells were propagated in Dulbecco's modified Eagle's medium containing 4.5 g/L glucose, 10% (v/v) fetal calf serum (FCS), and 50 mg/ml gentamycin sulfate (DMEM/10F). The cells were grown at 37° C. in a humidified incubator in the presence of 7% $CO_2$. The cells were passaged as instructed in the ATCC directions supplied with the cells.

In order to prepare cells for infection, the cells were washed with a normal saline solution containing 0.05% trypsin and 0.02% EDTA (STV), and removed from the tissue culture flasks by digestion with a small volume of STV. The Hep G2 cells in STV were diluted at least 10 fold in fresh DMEM/10F, and plated in order to achieve approximately 80% confluence following attachment.

On the following day, the cells were observed by microscope to verify that they were close to or were confluent, and the medium was removed. The cells were washed one time with MCDB-302 medium, see McKeehan, et al., Biochem. Biophys. Res. Comm. 80:1013 (1978), fresh MCDB-302 medium was added, and the cells were cultured overnight. The following day, the medium was replaced with fresh MCDB -302 medium, and the cells were infected with HCV.

In order to detect viral growth, $1\times10^6$ Hep G2 cells per well were cultured as described above, using a 6-well tissue culture dish (Falcon; growth area=approximately 35 mm diameter) in 3 ml medium. The Hep G2 cells were infected with $10^5$ chimp infectious doses (CID) of HCV present in 100 µl plasma from an HCV infected chimp; alternatively, human plasma from a HCV-seropositive individual was used for infection. On day 3 post-infection, the medium was replaced with 3 ml Eagle's minimum essential medium minus methionine and cysteine (MEM (−Met, Cys)) and the cells were incubated for 1 hr. The medium was then replaced with MEM (−Met, Cys) supplemented with 0.25 mC each of $^{35}$S-Met and $^{35}$S-Cys, and the cells were incubated for 4 hr in order to radioactively label newly synthesized proteins.

Following labelling, the cells were washed with Dulbecco's phosphate buffered saline solution (PBS), and the cells were lysed in 1 ml of lysis buffer containing 100 mM NaCl, 50 mM Tris-HCl, pH 7.5, 0.1 mM EDTA, 0.5% NP40, 0.5% sodium dodecylsulfate (SDS) and 100 µg/ml aprotinin. The nuclei and insoluble proteins were removed by centrifugation at 14,000 rpm for 5 min in an Eppendorf centrifuge, and the lysates were either analyzed immediately, or stored frozen at −80° C. until used.

In order to detect HCV encoded proteins, the radiolabeled proteins from infected cell lysates were incubated with human antibodies from an HCV-seropositive individual with chronic hepatitis C. The incubation was for 16 hrs at 4° C. Antibodies in 15 µl of human immune serum were bound to 15 µl of protein-A Sepharose beads by incubation at 4° C. for 4 hours on a rotating shaker. Antibodies against cellular proteins present in the immune serum were blocked by incubation of the protein-A Sepharose bound antibodies for 8 hrs with 1 ml lysate from $2\times10^6$ unlabelled, uninfected Hep G2 cells in order to reduce background.

Following the blocking, the beads were washed twice with lysis buffer, and then incubated for 16 hours at 4° C. with the radio-labelled cell lysates on a rotating shaker. Following binding of the radiolabeled proteins, the protein A-Sepharose beads were washed 4 times with 1 ml of lysis buffer with intervening pelleting and resuspension. The proteins were then eluted from the beads using Laemmli sample buffer, and analyzed by slab gel SDS-polyacrylamide gel electrophoresis, using the conditions described by Laemmli, Nature 227:680 (1970). After electrophoresis, the gels were fixed and impregnated with EnHance (Du Pont) according to the manufacturer's directions; the gels were then dried and subjected to autoradiography. Controls for the study were uninfected Hep G2 cells.

The autoradiographs of the Hep G2 cells showed that novel bands corresponding to newly synthesized proteins were seen only in the Hep G2 cells that had been exposed to HCV. Since these bands were not present in the control Hep G2 cells, and because the serum used to precipitate them had been extensively blocked with lysate from uninfected cells, the polypeptides in the radiolabeled bands are most likely newly synthesized HCV antigens derived from virus that replicated in the HCV-infected Hep G2 cell line. An examination of the media from the infected cells and control cells yielded essentially the same results.

The replication of HCV in Hep G2 cells may also be established and corroborated by an examination of putatively infected cells and the cell mezum after infection for the presence of HCV RNA. After infection of the cells as described above, newly synthesized HCV RNA can be labelled with $^{32}$P-orthophosphate. Prior to labelling, the cells are grown in phosphate-free medium for about 1 hour, and then labelled with 1 mC per well of $^{32}$P-$P_i$ in phosphate-free MEM. The time at which the labelling is to be done is determined by quantitative PCR analysis of the HCV present in the infected cells or post-infection cell medium. When desirable, suppression of cellular RNA synthesis is accomplished by including sufficient actinomycin D in the incubation medium to reduce cellular RNA synthesis to approximately 3% to 5% of its normal level. Subsequent to labelling, the presence of viral RNA is detected by Southern Blot analysis. HCV cDNAs are blotted onto nitrocellulose filters and probed with the samples containing putative HCV RNAs. Hybridization is carried out under stringent conditions.

D. Propagation of HCV in a Transfected Hepatic Cell Line HUH7

1. Material and Methods

Cells. HUH7 cells were grown in a defined medium (HAM-12 minimal medium supplemented with growth factors and antibiotics) with or without 10% fetal calf serum. RNA was transfected into HUH7 cells using lipofection (BRL) as described by Yoo et al., *Virology* (1992) 191:889–899.

Preparation of RNA. Full-length and subgenomic HCV RNA was transcribed by T7 polymerase as shown in FIG. 1 from an expression vector p73HCF$_F$ and T$_7$HCV$_{s(7)}$, respectively, using a transcription kit (Promega).

Labeling of HCV RNA and RNA-RNA slot blot hybridization. For in Vivo labeling, cells were incubated with 0.2 mCi $^3$H-uridine (Amersham) in defined medium for 24 hours and total RNA was extracted. For in vitro labeling, $^3$H-UTP was included in the transcription reaction. Each labeled RNA was hybridized as a probe to 1 µg of unlabeled positive or negative HCV RNA which was immobilized on filter. Hybridization was carried out in 50% formamide, 5 ×SSC, 10 ×Denhardt, 50 mM phosphate buffer (pH 7), 0.1% SDS, 50 µg/ml of yeast RNA at 50° C. overnight. Each filter was washed with 2 ×SSC, 0.1% SDS at 20° C. for 15 minutes. The final wash was in 0.1 ×SSC, 0.1% SDS at 70° C. for 30 minutes.

Detection of HCV RNA by strand specific RT-PCR. RNA was converted into cDNA using JH51 (SEQ ID NO: 1) (nucleotide 251 to 269 as shown in Han et al., *PNAS (USA)* (1991) 88:1711–1715) for the detection of positive strand RNA or using JH178 (SEQ ID NO: 2) (nucleotides 29 to 46) for negative strand-RNA. The cDNAs were amplified as described in Han et al. supra. The resultant DNAs were analyzed by Southern blot hybridization using $P^{32}$-labeled Alx 89 (SEQ ID NO: 3) as a probe.

2. Experimental

The full-length HCV RNA with a positive polarity ($_R$+HCV$_F$) was transcribed by T7 polymerase from a transcription vector as shown in FIG. 1A. Previous translation studies where the 5' UTR of HCV RNA was linked to the CAT reporter gene showed that full-length HCV RNA is an inefficient template for translation (Yoo et al., supra; Selby et al., *J. Gen. Virol.* (1993) 74:1103–1113). Because subgenomic HCV RNA ($_R$+HCV$_S$, lacking 144 nucleotides at the 5' end as shown in FIG. 1C) was shown to be more translationally active than the full-length RNA, both RNAs were included in our transfection. Following the co-transfection with both $_R$+HCV$_F$ and $_R$+HCV$_S$, HUH7 cells were grown in a defined medium with or without fetal calf serum.

Figure 2:
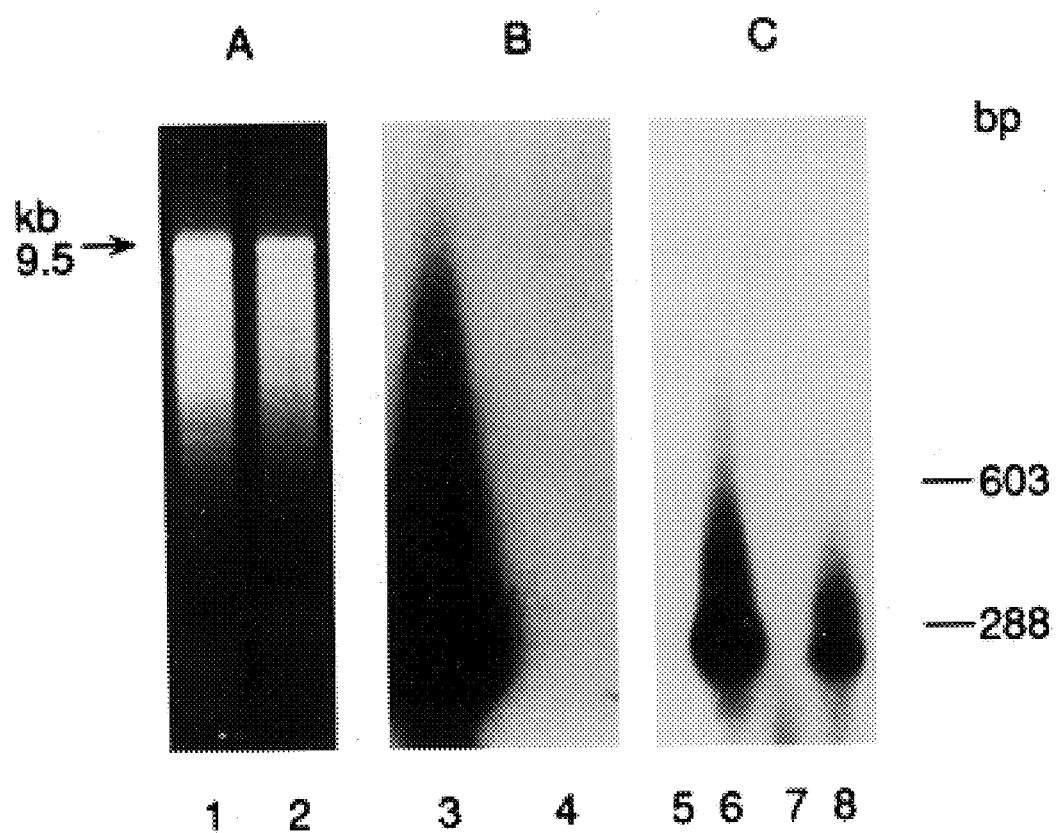
FIG. 2 shows an electrophoretic analysis of HCV RNA. (A) shows positive-strand HCV RNA transcribed by T7 polymerase in vitro. $_{R+}HCVF_F$ (lane 1) and $_{R+}HCV_S$ (lane 2) were electrophoresed in a 1.5% agarose gel and stained with ethidium bromide. (B) shows amplification of control HCV RNA by positive-strand (lane 3) or negative-strand specific RT-PCR (lane 4). (C) shows synthesis of HCV RNA in HUH7 cells detected by RT-PCR. Transfected (lanes 6 and 8) or mock transfected cells (lanes 5 and 7) were analyzed for the presence of positive (lanes 5 and 6) and negative strand HCV RNA (lanes 7 and 8) by strand specific RT-PCR.
Figure 3:
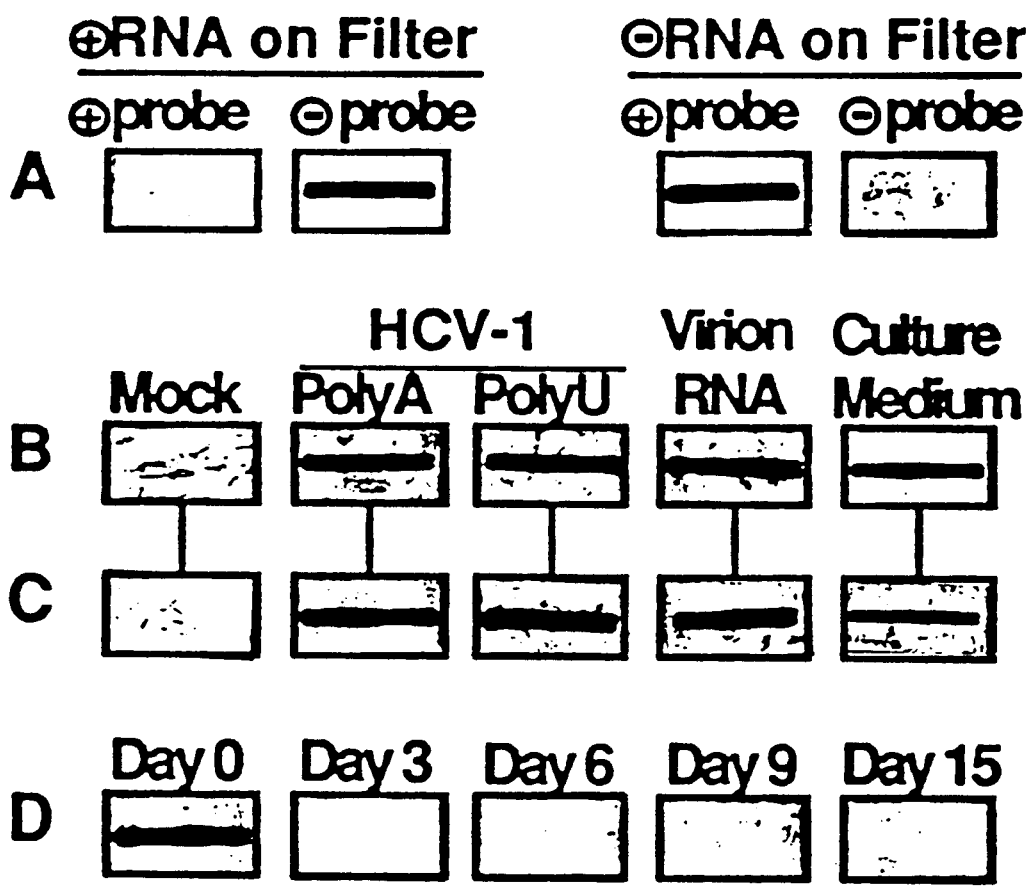
FIG. 3 shows RNA—RNA slot blot hybridization detection of in vitro incorporation of $^3$H-uridine into HCV RNA. (A) shows hybridization of in vitro $^3$H-UTP labeled positive- or negative-strand HCV RNA as a probe with 1 ug of unlabeled positive- or negative-strand HCV RNA immobilize on a cellulose nitrate filter. (B) shows hybridization of in vivo labeled positive-strand HCV RNA isolated from cells which were transfected or infected with the indicated source as a probe to 1 ug of unlabeled HCV RNA on filter. (C) shows hybridization of same in vivo labeled RNA to unlabeled positive strand RNA on filter. (D) shows hybridization of cellular RNAs isolated (at indicated days after transfection) from HUH7 cells transfected with the in vitro labeled positive-strand subgenomic RNA to negative-strand HCV RNA on filter.

Biological activity of the synthetic full-length HCV RNA was assessed as shown in FIG. 2. Approximately $1 \times 10^6$ HUH7 cells were transfected with 1 ug each of the full-length and the subgenomic HCV RNA. Two weeks after the transfection, cytoplasmic RNA from approximately $1 \times 10^5$ transfected or mock transfected cells were analyzed for the presence of positive and negative strand HCV RNA by strand specific RT-PCR, as shown in FIG. 2C. (Approximately $10^7$ molecules of positive-strand internal control RNA (Weiner, A. J. et al., *Diagnosis of Human Viruses by Polymerase Chain Reaction Technology* (1992) (ecker, Y. and Darai, G. Eds.) Splinger-Verlag, New York, pgs 86–100) was converted into cDNA and amplified by PCR as well.) The detection of intracellular HCV RNAs, especially the negative-stand RNA, was an indication of viral replication from the transfected RNA, since the negative strand HCV RNA was absent in the synthetic RNA preparation, as seen in FIGS. 2B and 3A. In addition, HCV RNA, presumably derived from secreted virus was also detected in post-transfection culture medium, often after an eclipse period as shown below.

The replication of transfected viral RNA was also evidenced by testing for the specific de novo incorporation of $^3$H-uridine into HCV RNA As shown in FIGS. 3B and C, when HUH7 cells were labeled with $^3$H-uridine two weeks after co-transfection and probed with cellular RNA as a probe in a RNA—RNA dot blot hybridization, we detected radioactivity in both strands of HCV RNA. In contrast, transfection of HUH7 cells with the subgenomic $_R$+HCV$_S$ RNA alone resulted in rapid degradation 3 days post-transfection and both strands of HCV RNA were undetectable thereafter, as seen in FIG. 3D. These data indicate the de novo synthesis of HCV RNA has resulted from the transfection of the full-length $_R$+HCV$_F$ RNA into HUH7 cells.

Culture supernatants collected from transfected cells, which were PCR positive were tested for the presence of infectious HCV virus particles. For this purpose, a PCR positive culture supernatant (14 days post-co-transfection) was filtered through a membrane (Millipore, 0.22 um), inoculated with fresh HUH7 cells, and assayed for $^3$H-uridine incorporation. As shown in FIG. 3B, labeled HCV RNA was detected in fresh cells. This result suggests that HCV RNA transfection gives rise to infectious replicating viruses. HUH7 cells were then transfected with virion RNA isolated from patient plasma. This HCV RNA, although present at picogram range, also resulted in $^3$H-uridine incorporation into both strands of HCV RNAs at a level comparable to that seen in the synthetic RNA which was present at microgram range, as shown in FIGS. 3B and C.

HCV-1 RNA has a poly (A) tail (Han et al. supra) but HCV RNA of other isolates have a poly (U) tail at the 3' end of the genome (Kato et al., *PNAS (USA)* (1990) 87:9524–9528). The effect of different homopolymer tails on viral replication was investigated. The poly (A) tail in the context of HCV-1RNA (FIG. 1B) was substituted with poly (U) and the co-transfection experiment was repeated. Using $^3$H-uridine incorporation, no qualitatively significant difference between the two RNAs was detected, as shown in FIGS. 3B and C.

Figure 4:
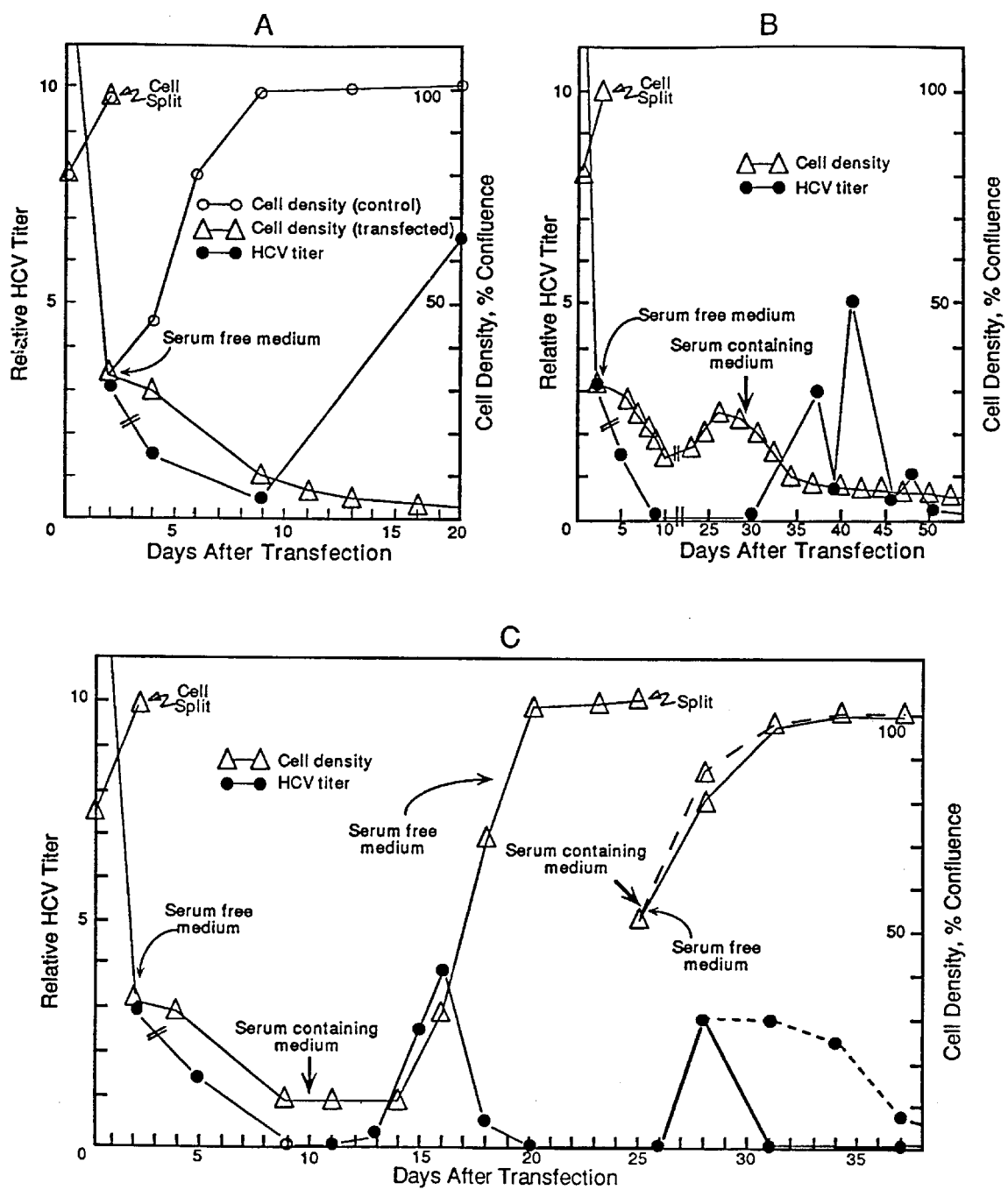
FIG. 4 shows a profile of HCV RNA accumulation in culture medium. (A) Accumulation of HCV RNA in serum-free medium (changed once at day 9). (B) Accumulation of HCV RNA in serum-free medium changed every 3 days. (C) Accumulation of HCV RNA in alternating serum-free and serum-containing medium changed every 3 days. Positive strand HCV RNA was analyzed by semi-quantitative RT-PCR.

The ability of HCV infection to be maintained as a long term culture in transfected HUH7 cells was investigated. HUH7 cells were split into three plates 3 days after HCV RNA co-transfection, as seen in FIGS. 4A–C. When one plate of cells were continuously maintained in serum-free medium, the cell density declined progressively, although a low level of PCR signal was detectable in the medium at day 9 (FIG. 4A). The density of transfected cells further declined even after a medium change at day 9 and most cells eventually died at day 20. The medium collected on day 20 bad a PCR signal 12 times higher than that seen in medium collected at day 9 (FIG. 4A). When cells in the second plate were grown in serum-free medium with frequent medium changes (once every 3 days), the cell density fluctuated between 15% and 30% confluent without detectable HCV titer in the medium between day 10 and day 30 (FIG. 4B). This resulted in a complete recovery of cell growth. In order to keep the cells from outgrowing the virus replication, cells were maintained in serum-free and serum-containing medium in an alternating manner (FIG. 4C). Using these conditions, the first detectable PCR signal was found at day 13 and peaked at day 16, which coincided with exponential cell growth. This peak in HCV titer was followed by a sharp decline and a loss of signal at day 20, during which cells entered stationary phase. Upon passage of these cells at day 25, the pattern of cell growth and accumulation of HCV RNA in the medium was repeated. However, in the second cycle, the HCV signal persisted longer when the split cells were maintained in serum-containing medium (dotted curve of FIG. 4C). This result and the data shown in FIG. 4B suggest that HCV replication (secretion) could be induced by serum, independent of cell division.

Figure 5A:
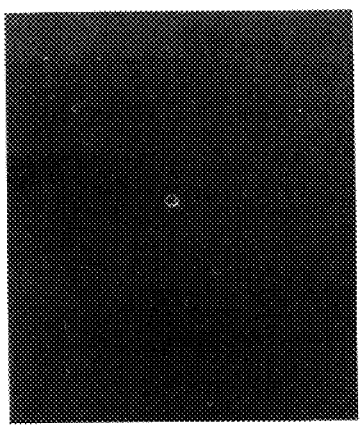
FIG. 5 shows long term cultures of HUH7 clones infected with HCV. (A) shows HUH7 cell survived from cell death after transfection. (B) shows growth pattern of the survived HUH7 cells at low density. (C) shows an established clone at 40 days after transfection. (D) shows a confluent monolayer of uninfected HUH7 cells. (E) shows uninfected HUH7 cells at low density. (F) shows morphology of the established clone at a higher magnification.
Figure 5B:
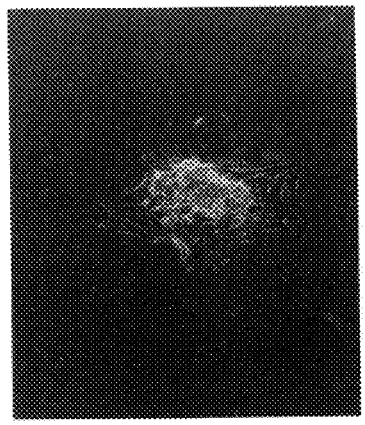
Figure 5C:
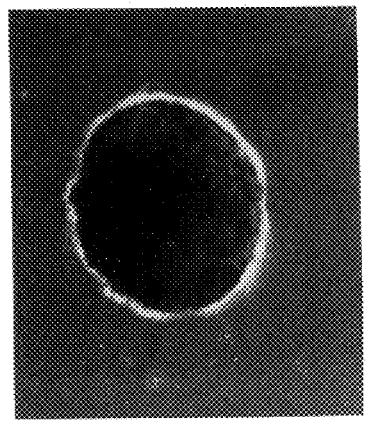
Figure 5D:
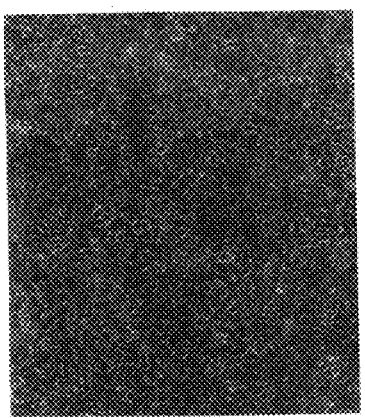
Figure 5E:
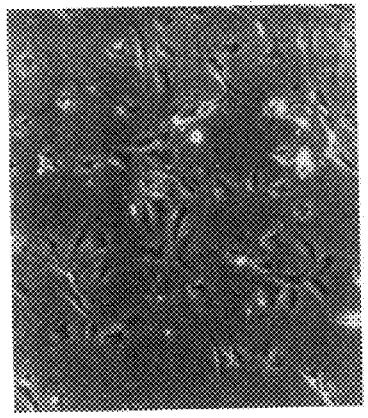
Figure 5F:
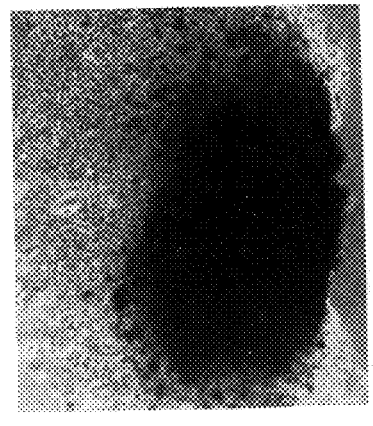

Repeated plating of transfected cells mainly in serum-free media generally resulted in cell death. Approximately two months after the transfection, a few surviving cells exhibited distinctive morphology, as shown in FIG. 5. These cells gave rise to visible colonies, some of which originated presumably from a single cell as exemplified in FIG. 5A. These cells within the colony were morphologically distinct from that of uninfected HUH7 cells in that they were smaller, round, and piled up as if they had lost contact inhibition (FIGS. 5B and C). The uninfected control HUH7 cells grew as a monolayer (FIG. 5D and E). One of several cell lines, which can be maintained in serum-free medium for at least 4 months after transfection, produced HCV in medium at varying titers. At its peak it produced an HCV titer at approximately $10^5$ genome copies/ml medium.

What is claimed is:

1. A method of preparing a composition for the detection of an anti-HCV antibody which comprises:

purifying or partially purifying HCV virus particles or polypeptides from a cell line infected with HCV, wherein the cells in the cell line are B lymphocytes or T lymphocytes, and are capable of replicating HCV; and fixing said particles or polypeptides to a solid phase.

2. A method according to claim 1, wherein the cells in the cell line are B lymphocytes.

3. A method according to claim 1, wherein the cells in the cell line are T lymphocytes.

4. A method according to claim 1, wherein said HCV particles or polypeptides are solubilized with a detergent.

5. A method according to any of claims 1–4, wherein the composition for the detection of anti-HCV antibodies is packaged in a suitable container to provide a test kit.

* * * * *